United States Patent
Bombardelli et al.

(10) Patent No.: US 10,016,478 B2
(45) Date of Patent: Jul. 10, 2018

(54) COMBINATIONS OF EXTRACTS OF SERENOA REPENS AND LIPOPHILIC EXTRACTS OF ZINGIBER OFFICINALIS AND ECHINACEA ANGUSTIFOLIA, THE USE THEREOF, AND FORMULATIONS CONTAINING THEM

(71) Applicant: Indena S.P.A., Milan (IT)

(72) Inventors: Ezio Bombardelli, Gropello Cairoli (IT); Paolo Morazzoni, Milan (IT)

(73) Assignee: Indena S.P.A., Milan (IT)

( * ) Notice: Subject to any disclaimer, the term of this patent is extended or adjusted under 35 U.S.C. 154(b) by 0 days.

(21) Appl. No.: 15/626,203

(22) Filed: Jun. 19, 2017

(65) Prior Publication Data

US 2017/0281708 A1    Oct. 5, 2017

Related U.S. Application Data

(62) Division of application No. 14/890,932, filed as application No. PCT/EP2014/059297 on May 7, 2014, now Pat. No. 9,730,974.

(30) Foreign Application Priority Data

May 16, 2013    (IT) .............................. MI2013A0807

(51) Int. Cl.
| | |
|---|---|
| A61K 36/9068 | (2006.01) |
| A61K 36/758 | (2006.01) |
| A61K 36/889 | (2006.01) |
| A61K 36/28 | (2006.01) |
| A61K 47/44 | (2017.01) |
| A61K 36/55 | (2006.01) |
| A61K 36/185 | (2006.01) |

(52) U.S. Cl.
CPC .......... *A61K 36/9068* (2013.01); *A61K 36/28* (2013.01); *A61K 36/758* (2013.01); *A61K 36/889* (2013.01); *A61K 47/44* (2013.01); A61K 36/185 (2013.01); A61K 36/55 (2013.01); A61K 2236/00 (2013.01)

(58) Field of Classification Search
CPC .. A61K 36/889; A61K 36/9068; A61K 36/14; A61K 36/28

USPC .......... 424/727, 737, 756, 770, 776
See application file for complete search history.

(56) References Cited

U.S. PATENT DOCUMENTS 6,039,950 A  *  3/2000  Khwaja ................ A61K 36/889
                                                    424/727
6,261,607 B1      7/2001  Newmark et al.

FOREIGN PATENT DOCUMENTS

| WO | 2009103477 A1 | 8/2009 |
| WO | 2010083967 A1 | 7/2010 |

OTHER PUBLICATIONS

Anonymous: New Chapter Zyflamend Prostate Health, Softgel:, Aug. 31, 2012.
Geavlete P., et al., Serenoa repens extract in the treatment of benign prostatic hyperplasia.:, Therapeutic Advances in Urology, Aug. 2011, vol. 3, No. 4, pp. 193-198.
Li-Chen Y., et al., "Polyphenolics composition of the leaves of Zanthoxylum bungeanum Maxim. grown in Hebei, China, and their radical scavenging activities", Journal of Agricultural and Food Chemistry, vol. 61, No. 8, Feb. 27, 2013 pp. 1772-1778.
Wilt T et al., :Serenoa repens for begnin prostatic hyperplasia.:, The Cochrane Database of Systematic Reviews 2002, No. 3, CD001423, 2002 pp. Frontpg.-42.
Yang Y., et al., "Zanthoxyli Fructus induces growth arrest and apoptosis of LNCaP human prostate cancer cells in vitro and in vivo in association with blockade of the AKT and AR signal pathways.", Oncology Reports, vol. 15, No. 6, Jun. 1, 2006 pp. 1581-1590.
Yumiko H., et al., "Sichuan pepper extracts block the PAK1/Cyclin D1 pathway and the growth of NF1-deficient cancer xenograft in mice", Cancer Biology & Therapy, vol. 5, No. 3, Mar. 1, 2006 pp. 305-309.
International Preliminary Report on Patentability of PCT/EP2014/059297 dated Aug. 31, 2015.
International Search Report and Written Opinion of PCT/EP2014/059297 dated Jul. 28, 2014.

\* cited by examiner

*Primary Examiner* — Christopher R Tate
*Assistant Examiner* — Deborah A Davis
(74) *Attorney, Agent, or Firm* — Silvia Salvadori, P.C.; Silvia Salvadori

(57) ABSTRACT

Disclosed are compositions containing an extract of *Serenoa repens*, a lipophilic extract of *Zingiber officinalis* and a lipophilic extract of *Echinacea angustifolia* or *Zanthoxylum bungeanum*.

5 Claims, No Drawings

COMBINATIONS OF EXTRACTS OF SERENOA REPENS AND LIPOPHILIC EXTRACTS OF ZINGIBER OFFICINALIS AND ECHINACEA ANGUSTIFOLIA, THE USE THEREOF, AND FORMULATIONS CONTAINING THEM

This U.S. non-provisional application is a divisional of U.S. patent application Ser. No. 14/890,932 filed on Nov. 13, 2015, which is a U.S. National Stage of PCT/EP2014/059297 filed on 7 May 2014, which claims priority to and the benefit of Italian Application No. MI2013A000807 filed on 16 May 2013, the contents of which are incorporated herein by reference in their entireties.

The present invention relates to the combination of an extract of *Serenoa repens* with a lipophilic extract of *Zingiber officinalis* and a lipophilic extract of *Echinacea angustifolia* or *Zanthoxylum bungeanum* which is useful in the treatment of urinary incontinence, the symptoms of benign prostate hypertrophy, prostatitis and prostatism, and pelvic pain.

PRIOR ART

Prostate hypertrophy, an age-dependent physiological event caused by a modified hormone ratio between androgens and oestrogens, is often characterised by a series of unpleasant events such as dysuria, pollakiuria and incontinence, associated with inflammatory states and pelvic pain. Many of the supposed symptoms associated with increased prostate volume also appear to be associated with bladder dysrhythmia, which is common in both men and women, and characterised by similar symptoms.

*Serenoa repens* extracts are widely used in the clinical and nutritional fields to treat the symptoms of benign prostate hypertrophy in men and urinary incontinence in women (Hale E. M. (1898). Saw palmetto (*Sabal serrulata, Serenoa Serrulata*): its History, Botany, Chemistry, Pharmacology, Provings, Clinical Experience and Therapeutical Applications. Philadelphia: Boericke and Taffel).

*Zingiber officinalis* extract is traditionally used to treat dyspepsia, nausea and vomiting and to a lesser extent indigestion, flatulence, diarrhoea, cough and inflammation. Gingerols, the active ingredients of the plant, interact with NFkB and TNF-α. They also control gastric voiding, with the related consequences on the digestion (Rhode J. Et al., BMC Complement. Altern. Med. 7, 44, 2007; El-Sharaki et al., Food Chem. Toxicol 47, 1584, 2009; Micklefield G. H. et al., Int. J. Clin. Pharmacol. Ther. 37, 341, 1999).

The extracts of this plant are particularly useful in the treatment of nausea.

DESCRIPTION OF THE INVENTION

It has now surprisingly been found that by combining *Serenoa repens* extract with a lipophilic extract of *Zingiber officinalis* and a lipophilic extract of *Echinacea angustifolia* or *Zanthoxylum bungeanum*, the urogenital symptoms of both men and woman regress completely, with a rapid reduction of inflammation in prostatism and pelvic pain in general which has never been observed with the sole use of the extracts administered individually.

The present invention therefore relates to compositions containing a *Serenoa repens* extract, a lipophilic extract of *Zingiber officinalis* and a lipophilic extract of *Echinacea angustifolia* or *Zanthoxylum bungeanum*.

The invention also relates to said compositions for use in the treatment of urinary incontinence, benign prostate hypertrophy, prostatitis and prostatism, and pelvic pain.

*Serenoa repens* extract, which is rich in fatty acids, lipophilic extract of *Zingiber officinalis* and lipophilic extract of *Echinacea angustifolia* or *Zanthoxylum bungeanum* are preferably obtained by extraction with carbon dioxide under supercritical conditions.

The *Zingiber officinalis* extract used in the present invention, prepared by extraction from the rhizomes with carbon dioxide under supercritical conditions, is characterised by the fact that it contains 20 to 35% gingerols, preferably 25%.

The *Serenoa repens* extracts according to the invention contain between 60 and 90% fatty acids, preferably about 80%. The extracts can also be prepared with solvents selected from hexane, ethanol and acetone. Alternatively, the extract obtained by pressing the fresh fruit can be used. An example of a lipophilic extract of *Serenoa* is disclosed in EP 0250953.

The lipophilic extracts of *Echinacea angustifolia* or *Zanthoxylum bungeanum* contain between 15 and 35%, preferably 25%, of isobutylamides, and are prepared with carbon dioxide under supercritical conditions as reported in EP 0464298 and WO 00/02570. Isobutylamides are ligands of the cannabinoid receptors, particularly CB2, and agonists of TRPV1, the vanilloid receptor with a painkilling function.

The extracts of *Serenoa repens*, *Zingiber officinalis* and *Echinacea angustifolia* or *Zanthoxylum bungeanum* are preferably present in the compositions according to the invention in the ratios of 1:0.25-0.5:0.05-01, which minimise the side effects and consequently allow safe chronic treatment.

The therapeutic effect was evaluated on the basis of internationally accepted scores according to the NIH-CPSI (National Institute of Health-Chronic Prostatitis Symptoms Index) which monitors CP-CPPS (chronic prostatitis/chronic pelvic pain syndrome), which is associated with urinary symptoms such as pollakiuria, dysuria, nocturia and sexual dysfunctions which have lasted for at least three to six months and are present in the absence of urogenital infections, tumours or anatomical abnormalities. The evaluations are functional in the absence of specific markers, and require an adequate number of patients. The scale comprises an NIH-CPSI range of 0 to 43 (43 for the most serious cases). A population with variations of 0 to 30 in the inclusion criteria was evaluated.

The trial was carried out on 80 patients aged between 55 and 70 years (63±7) with category IIIB CPPS. The patients were divided into 4 groups after randomisation; the first group was treated with capsules of *Serenoa repens* lipophilic extract (120 mg, 3 capsules a day), the second with the combination described in example 1 (3 capsules a day), the third with the mixture of *Echinacea angustifolia/Zingiber officinalis* lipophilic extract (3 capsules a day) prepared as described in EP 2379095 and administered in groundnut oil, and the fourth with a placebo. The data are reported in Table 1.

TABLE 1

Variations in NIH-CPSI for pelvic pain and quality of life after treatment with Combination 1 and the ingredients thereof

|  |  | NIH-CPSI TOTAL | NIH-CPSI PAIN | NIH-CPSI QUALITY OF LIFE |
|---|---|---|---|---|
| *Serenoa repens* | Start | 23.1 (1.8) | 9.8 (1.6) | 8.0 (0.9) |
|  | 3 months | 14.3 (1.3) | 7.3 (1.1) | 3.8 (1.1) |
|  | 6 months | 10.2 (1.1) | 6.5 (1.2) | 4.5 (0.8) |

TABLE 1-continued

Variations in NIH-CPSI for pelvic pain and quality of life after treatment with Combination 1 and the ingredients thereof

|  |  | NIH-CPSI TOTAL | NIH-CPSI PAIN | NIH-CPSI QUALITY OF LIFE |
|---|---|---|---|---|
| Combination 1 | Start | 22.4 (1.5) | 9.7 (1.5) | 7.8 (0.9) |
|  | 3 months | 11.3 (1.1) | 3.2 (1.0) | 2.2 (0.9) |
|  | 6 months | 8.2 (1.2) | 1.5 (1.1) | 2.1 (0.8) |
| Echinacea/ginger | Start | 22.7 (11.4) | 9.1 (1.1) | 7.9 (1.2) |
|  | 3 months | 17.4 (1.5) | 8.2 (1.2) | 6.2 (1.1) |
|  | 6 months | 12.6 (1.4) | 7.3 (1.1) | 6.2 (1.1) |
| Placebo | Start | 24.2 (1.7) | 9.2 (1.3) | 7.6 (1.1) |
|  | 3 months | 15.1 (1.6) | 7.3 (1.2) | 6.9 (0.8) |
|  | 6 months | 11.2 (1.5) | 6.5 (1.1) | 5.9 (1.0) |

A second group of 60 patients was treated similarly to the first, evaluating the changes in the IPSS (International Prostate Symptom Score) and quality of life; the *Serenoa repens* extract, the combination and the placebo were compared for six months. The results are reported in Table 2.

TABLE 2

|  | Start | 2 months | 4 months | Final | MODIFICATIONS |
|---|---|---|---|---|---|
| SYMPTOMS (score) |  |  |  |  |  |
| *Serenoa repens* | 16.5 ± 4.7 | 12.9 ± 4.4 | 11.9 ± 5.0 | 12.1 ± 5.3 | −4.4 ± 5.0 ($p < 0.036$) |
| Combination 1 | 17.1 ± 4.6 | 9.5 ± 4.2 | 8.6 ± 5.2 | 7.6 ± 5.8 | −9.5 ± 5.2 ($p < 0.001$) |
| Placebo | 15.9 ± 4.5 | 12.3 ± 5.2 | 13.2 ± 5.3 | 13.5 ± 6.4 | −2.4 ± 5.4 |
| QUALITY OF LIFE (score) |  |  |  |  |  |
| *Serenoa repens* | 3.3 ± 1.2 | 3.1 ± 1.3 | 2.7 ± 1.1 | 2.6 ± 1.4 | −0.7 ± 1.3 |
| Combination 1 | 3.2 ± 1.2 | 2.8 ± 1.1 | 2.0 ± 1.2 | 1.8 ± 1.1 | −1.4 ± 1.1 ($p < 0.05$) |
| Placebo | 3.1 ± 1.2 | 2.9 ± 1.0 | 2.8 ± 1.2 | 2.8 ± 1.1 | −0.3 ± 1.1 |

Values expressed as mean ± S.D.
$p < 0.05$ (significance vs. placebo)

The results of the studies demonstrate the synergy of the composition compared with the individual ingredients.

The pharmaceutical compositions mainly take the form of soft gelatin or cellulose capsules suitable for oils that disperse rapidly in the stomach, or capsules or tablets after microencapsulation of the oils.

A preferred lipophilic formulation uses as dispersing agent oils rich in ω-3 fatty acids, which promote rapid absorption of the active ingredient. Examples of said oils include *Oenothera biennis* oil, *Linum usitatissimum* oil and *Ribes nigrum* oil, and natural or semi-synthetic fish oils. Said compositions are mainly used in curative and maintenance treatments, and to reduce pelvic pain.

According to a preferred aspect, the compositions according to the invention will also contain antioxidants, such as palmitoyl ascorbate, catechin and gallic polyphenols, or lycopene and extracts containing it, and trace elements such as zinc, selenium and manganese.

These compositions can be prepared according to conventional methods, as described in "Remington's Pharmaceutical Handbook", Mack Publishing Co., N.Y., USA, using suitable excipients. Some formulation examples are reported below.

Example 1—Soft Gelatin Capsules

| *Serenoa repens* extract | 120 mg |
|---|---|
| *Zingiber officinalis* lipophilic extract | 25 mg |
| *Echinacea angustifolia* lipophilic extract | 5 mg |
| Soya lecithin | 10 mg |
| Palmitoyl ascorbate | 20 mg |
| *Oenothera biennis* lipophilic extract | 150 mg |

Example 2—Cellulose Capsules for Oils

| *Serenoa repens* extract | 120 mg |
|---|---|
| *Zingiber officinalis* lipophilic extract | 50 mg |
| *Echinacea angustifolia* lipophilic extract | 10 mg |
| Soya lecithin | 10 mg |
| *Oenothera biennis* lipophilic extract | 150 mg |

Example 3—Tablets

| *Serenoa repens* extract | 120 mg |
|---|---|
| *Zingiber officinalis* lipophilic extract | 50 mg |
| *Echinacea angustifolia* lipophilic extract | 10 mg |
| Soya lecithin | 10 mg |
| Palmitoyl ascorbate | 20 mg |
| *Oenothera biennis* lipophilic extract | 150 mg |

Example 4—Soft Gelatin Capsules

| *Serenoa repens* extract | 130 mg |
|---|---|
| *Zingiber officinalis* lipophilic extract | 25 mg |
| *Echinacea angustifolia* lipophilic extract | 5 mg |
| Soya lecithin | 10 mg |
| Palmitoyl ascorbate | 20 mg |
| *Lycopersicon aesculentum* extract (10% lycopene) | 50 mg |
| *Oenothera biennis* lipophilic extract | 150 mg |

Example 5—Soft Gelatin Capsules

| | |
|---|---|
| *Serenoa repens* extract | 120 mg |
| *Zingiber officinalis* lipophilic extract | 25 mg |
| *Zanthoxylum bungeanum* lipophilic extract | 5 mg |
| Soya lecithin | 10 mg |
| Palmitoyl ascorbate | 20 mg |
| *Oenothera biennis* lipophilic extract | 150 mg |

The invention claimed is:

1. A composition for treating urinary incontinence, prostate hypertrophy, prostatitis, prostatism, and/or pelvic pain, said composition comprising a *Serenoa repens* extract, a *Zingiber officinalis* lipophilic extract and an *Echinacea angustifolia* or *Zanthoxylum bungeanum* lipophilic extract, wherein the *Serenoa repens* extract: *Zingiber officinalis* lipophilic extract: *Echinacea angustifolia* or *Zanthoxylum bungeanum* lipophilic extract ratios are 1:0.25-0.5:0.05-0.1.

2. The composition according to claim 1 wherein the extracts of *Serenoa repens, Zingiber officinalis, Echinacea angustifolia* and *Zanthoxylum bungeanum* are prepared by extraction with supercritical carbon dioxide.

3. The composition according to claim 1 further comprising oils rich in $\omega$-3 fatty acids.

4. The composition according to claim 3 wherein the oils are selected from *Oenothera biennis, Linum usitatissimum* or *Ribes nigrum* oils and natural or semi-synthetic fish oils.

5. The composition according to claim 1 further containing antioxidants and trace elements.

* * * * *